US006475529B2

(12) United States Patent
Duponchelle et al.

(10) Patent No.: US 6,475,529 B2
(45) Date of Patent: Nov. 5, 2002

(54) BICARBONATE-BASED SOLUTION IN TWO PARTS FOR PERITONEAL DIALYSIS OR SUBSTITUTION IN CONTINUOUS RENAL REPLACEMENT THERAPY

(75) Inventors: Annick Duponchelle, Brussels (BE); Dirk Faict, Assenede (BE); Patrick Balteau, Bothey (BE); Jean-Pierre Hartman, Rhode-St-Genèse (BE); Leo Martis, Long Grove, IL (US); Francesco Peluso, Heverlee (BE)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/918,328

(22) Filed: Jul. 30, 2001

(65) Prior Publication Data

US 2002/0012707 A1 Jan. 31, 2002

Related U.S. Application Data

(62) Division of application No. 09/393,743, filed on Sep. 10, 1999, now Pat. No. 6,309,673.

(51) Int. Cl.[7] ...................... A61K 33/00; A61K 31/045; A61K 31/19; A61K 31/70; A61K 47/00; A61J 1/00; A61L 2/07

(52) U.S. Cl. ...................... 424/717; 206/219; 206/438; 206/439; 220/500; 422/1; 422/26; 422/28; 422/38; 422/41; 424/677; 424/678; 424/680; 424/681; 424/682; 424/722; 514/23; 514/557; 514/724; 514/769; 514/777; 514/784; 604/403; 604/410; 604/416

(58) Field of Search ................................ 424/677, 678, 424/679, 680, 681, 682, 686, 717, 722; 514/2, 25, 54, 60, 557, 561, 738, 777, 773, 778, 784, 788, 724, 769; 206/219, 438, 439; 220/500; 422/1, 26, 28, 38, 41; 604/403, 410, 416

(56) References Cited

U.S. PATENT DOCUMENTS

| 4,396,383 A | 8/1983 | Hart ............................ 604/518 |
| 4,465,488 A | 8/1984 | Richmond et al. ........... 604/414 |
| 4,489,535 A | 12/1984 | Veltman ....................... 53/431 |
| 4,584,176 A | 4/1986 | Oliver et al. ................. 422/41 |
| 4,630,727 A | 12/1986 | Feriani et al. ............... 206/221 |

(List continued on next page.)

FOREIGN PATENT DOCUMENTS

| DE | 19748290 | 5/1999 |
| EP | 0 083 360 | 7/1981 |
| EP | 0 165 933 B1 | 1/1986 |
| EP | 0 249 667 B1 | 12/1987 |
| EP | 0 278 100 | 6/1988 |

(List continued on next page.)

OTHER PUBLICATIONS

American Society for Artificial Internal Organs, 1994, Abstracts, pp. 110.
Faller et al., "Loss of Ultrafiltration in Continuous Ambulatory Peritoneal Dialysis: A Role for Acetate", Peritoneal Dialysis Bulletin, Jan.–Mar. 1984, pp 10–13.
Ing et al., "Lactate–Containing Peritoneal Dialysis Solutions", International J. of Artificial Organs, vol. 16, No. 10, 1993, pp. 688–693.
Ing et al., "Lactate–Containing Versus Bicarbonate–Containing Peritoneal Dialysis Solutions", Peritoneal Dialysis International, vol. 12, pp 276–277.
Ing et al., "Preparation of Bicarbonate–Containing Dialysate for Peritoneal Dialysis", International J. of Artificial Organs, vol. 6, No. 4, 1983, pp 217–218.
Manahan et al., "Effects of Bicarbonate–Containing Versus Lactate–Containing Peritoneal Dialysis Solutions on Superoxide Production by Human Neutrophils", Artificial Organs, vol. 13, No. 6, 1989, pp 495–497.
Richardson et al., "Bicarbonate, L–Lactate, and D–Lactate Balance in Intermittent Peritoneal Dialysis", Peritoneal Dialysis Bulletin, vol. 6, No. 4, 1986, pp 178–185.
Yatzidis, Hippocrates, "A New Stable Bicarbonate Dialysis Solution for Peritoneal Dialysis: Preliminary Report", Peritoneal Dialysis International, vol. 11, pp 224–227.
Boen ST, A Clinical Study of Factors Governing its Effectiveness, Peritoneal Dialysis, p. 76, Van Gorcum & Co., Assen. The Neterlands (1959).
Feriani et al., Short–Term Clinical Study with Bicarbonate–Containing Peritoneal Dialysis Solution, Peritoneal Dialysis International, vol. 13, pp. 296–301 (1993).
The Merck Index, 12th Ed., Merck Research Laboratories, Whitehouse Station, NJ, p. 1472, 1996.
Murphen et al., "Use of an Artificial Kidney," J. Lab. Clin. Med., vol. 40, pp. 436–444, 1952.
Odel HM et al., "Peritoneal Lavage as an Effective Means of Extrarenal Excretion. A Clinical Appraisal," Amerian J. of Medicine, vol. 9, pp. 63–68, 1950.

(List continued on next page.)

Primary Examiner—Jose' G. Dees
Assistant Examiner—Frank Choi
(74) Attorney, Agent, or Firm—Paula Kelly; Joseph Reagen; Robert M. Barrett

(57) ABSTRACT

The present invention provides devices and methods for stabilizing bicarbonate-based solutions for peritoneal dialysis or hemofiltration. The bicarbonate-based solutions of the present invention are formulated and stored in at least two parts—an alkaline bicarbonate concentrate and an acidic concentrate. The alkaline bicarbonate concentrate is adjusted to have a pH of about 8.6 to 10.0. The acidic concentrate is adjusted to have a stable, acidic pH ranging from about 1.0 to 3.0. Upon mixing, although some variation in the pH of the mixed bicarbonate solution exists, the inventors have discovered that with the appropriate selection of the parameters of the concentrates, the pH of the mixed solution is always within an acceptable physiological range.

14 Claims, 2 Drawing Sheets

U.S. PATENT DOCUMENTS

| | | | |
|---|---|---|---|
| 4,663,166 A | 5/1987 | Veech | 424/663 |
| 4,756,838 A | 7/1988 | Veltmann | 424/490 |
| 4,761,237 A * | 8/1988 | Alexander et al. | 210/647 |
| 4,863,714 A | 9/1989 | Sovak et al. | 424/9.45 |
| 4,879,280 A | 11/1989 | Seyffart et al. | 514/53 |
| 4,959,175 A | 9/1990 | Yatzidis | 252/364 |
| 5,011,826 A | 4/1991 | Steudle et al. | 514/23 |
| 5,039,609 A | 8/1991 | Klein | 435/68.1 |
| 5,141,492 A | 8/1992 | Dadson et al. | 604/28 |
| 5,211,643 A | 5/1993 | Reinhardt et al. | 604/416 |
| 5,296,242 A | 3/1994 | Zander | 424/717 |
| 5,383,324 A | 1/1995 | Segers et al. | 53/425 |
| 5,423,421 A | 6/1995 | Inoue et al. | 206/219 |
| 5,431,496 A | 7/1995 | Balteau et al. | 383/38 |
| 5,462,526 A | 10/1995 | Barney et al. | 604/85 |
| 5,509,898 A | 4/1996 | Isono et al. | 604/87 |
| 5,536,469 A | 7/1996 | Jonsson et al. | 422/1 |
| 5,560,403 A | 10/1996 | Balteau et al. | 141/9 |
| 5,610,170 A | 3/1997 | Inoue et al. | 514/340 |
| 5,706,937 A | 1/1998 | Futagawa et al. | 206/221 |
| 5,827,820 A * | 10/1998 | duMoulin et al. | 514/2 |
| 5,853,388 A | 12/1998 | Semel | 604/82 |
| 5,871,477 A | 2/1999 | Isono et al. | 604/410 |
| 5,945,129 A | 8/1999 | Knerr et al. | 424/676 |
| 6,277,815 B1 * | 8/2001 | Knerr | 514/2 |

FOREIGN PATENT DOCUMENTS

| | | |
|---|---|---|
| EP | 0 277 868 | 8/1988 |
| EP | 0 209 607 | 12/1989 |
| EP | 0 399 549 | 11/1990 |
| EP | 0 439 061 B1 | 7/1991 |
| EP | 0 613 688 A1 | 9/1994 |
| EP | 0 647 145 B1 | 4/1995 |
| EP | 0 776 649 A2 | 6/1997 |
| EP | 0 935 967 | 8/1999 |
| FR | 2753099 | 3/1998 |
| JP | 56164113 | 12/1981 |
| JP | 2304026 | 12/1990 |
| JP | 3195561 | 8/1991 |
| JP | 5105633 | 4/1993 |
| JP | 6105905 | 4/1994 |
| JP | 7252137 | 10/1995 |
| JP | 8131542 | 5/1996 |
| JP | 8164199 | 6/1996 |
| JP | 9087182 | 3/1997 |
| JP | 9110703 | 4/1997 |
| JP | 9301875 | 11/1997 |
| JP | 10201821 | 8/1998 |
| JP | 11-9659 | 1/1999 |
| JP | 11-19178 | 1/1999 |
| JP | 11004872 | 1/1999 |
| JP | 11019178 | 1/1999 |
| WO | 86/03407 | 6/1986 |
| WO | 87/03809 | 7/1987 |
| WO | 91/18610 | 12/1991 |
| WO | 95/19778 | 7/1995 |
| WO | 96/01118 | 1/1996 |
| WO | 97/05851 | 2/1997 |
| WO | 98/10733 | 3/1998 |
| WO | 99/01144 | 1/1999 |
| WO | 99/09953 | 3/1999 |

OTHER PUBLICATIONS

Schambye et al., "The Cytotoxicity of Continuous Ambulatory Peritoneal Dialysis Solutions with Different Bicarbonate/Lactate Ratios", Peritoneal Dialysis International, vol. 13, Suppl. 2, Oct. 1–4, pp. S116–S118, 1994.

Schambye et al., "Bicarbonate versus Lactate–Based CAPD Fluids: A Biocompatibility Study in Rabbits," Peritoneal Dialysis International, vol. 12, pp 281–286, 1992.

Simonsen et al., "Less Infusion Pain and Elevated Level of Cancer Antigen 125 by the Use of a New and More Biocompatible PD Fluid," Advances in Per. Dialysis, vol. 12, pp 156–160, 1996.

T.S. Ing et al., "Bicarbonate–Buffered Peritoneal Dialysis," The Intnl. J. of Artificial Organs, vol. 8, No. 3, pp 121–124, 1985.

Zhou et al., Effects of an Acidic, Lactate–Based Peritoneal Dialysis Solution and its Euhydric, Bicarbonate–Based Counterpart on Neutrophilic INtracellular pH, INt. J. Artif. Organs, vol. 16, No. 12, pp 816–819, 1993.

* cited by examiner

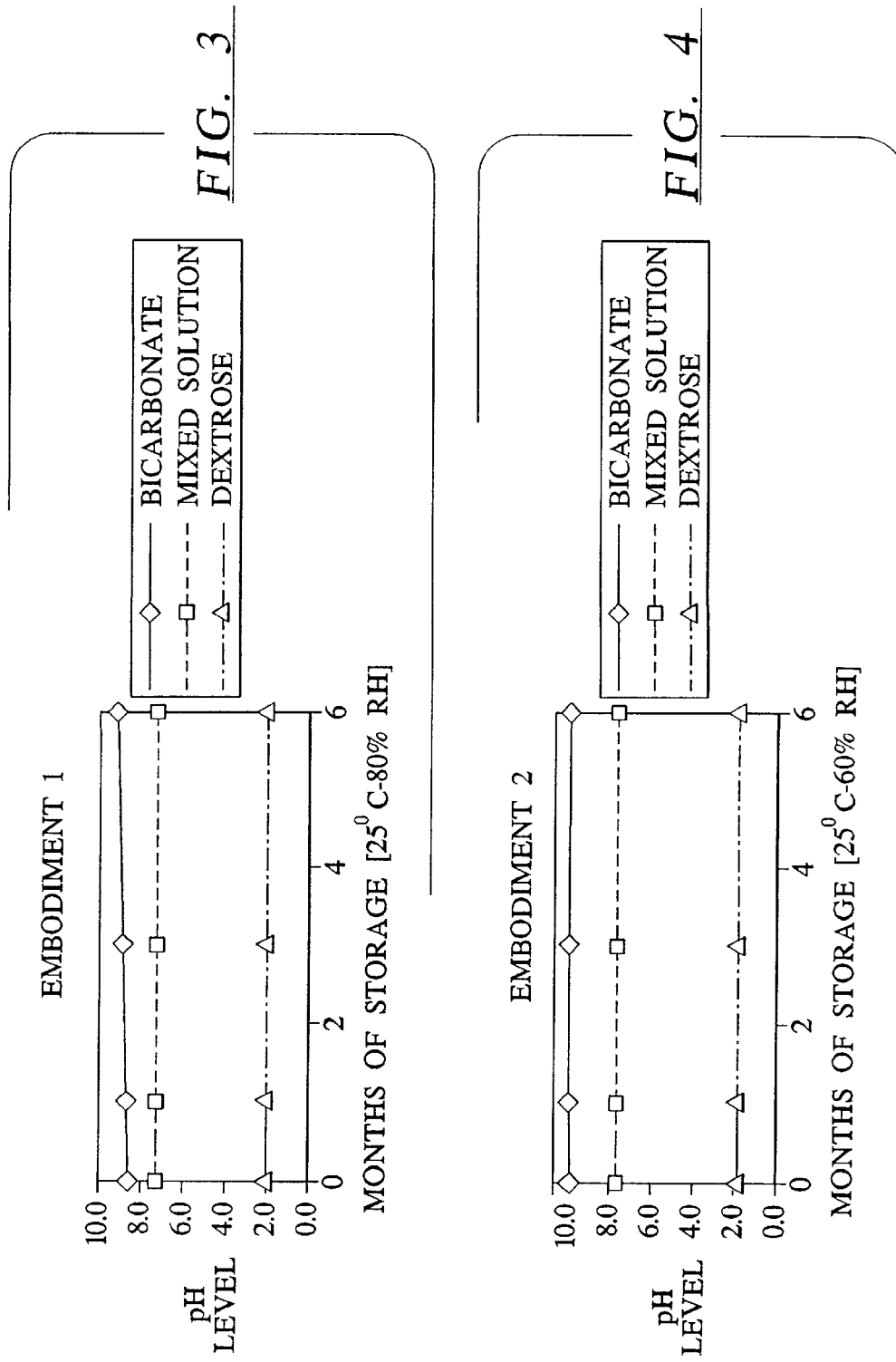

BICARBONATE-BASED SOLUTION IN TWO PARTS FOR PERITONEAL DIALYSIS OR SUBSTITUTION IN CONTINUOUS RENAL REPLACEMENT THERAPY

This application is a division of U.S. application Ser. No. 09/393,743, filed on Sep. 10, 1999, now U.S. Pat. No. 6,309,673.

BACKGROUND OF THE INVENTION

The present invention relates generally to peritoneal dialysis and renal replacement therapies, such as hemofiltration and hemodiafilitration. More specifically, the present invention relates to manufacturing and storing bicarbonate-based solutions for peritoneal dialysis and hemofiltration.

To overcome the disadvantages often associated with classical hemodialysis, other techniques were developed, such as peritoneal dialysis and hemofiltration. Peritoneal dialysis utilizes the patient's own peritoneum as a semipermeable membrane. The peritoneum is the membranous lining of the body cavity that, due to the large number of blood vessels and capillaries, is capable of acting as a natural semipermeable membrane.

In peritoneal dialysis, a sterile dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows a proper acid-base, electrolyte and fluid balance to be returned to the blood. The dialysis solution is simply drained from the body cavity through the catheter.

Hemofiltration is a convection-based blood cleansing technique. Blood access can be venovenous or arteriovenous. As blood flows through the hemofilter, a transmembrane pressure gradient between the blood compartment and the ultrafiltrate compartment causes plasma water to be filtered across the highly permeable membrane. As the water crosses the membrane, it convects small and large molecules across the membrane and thus cleanses the blood. An excessive amount of plasma water is eliminated by filtration. Therefore, in order to keep the body water balanced, fluid must be substituted continuously by a balanced electrolyte solution (replacement or substitution fluid) infused intravenously. This substitution fluid can be infused either into the arterial blood line leading to the hemofilter (predilution) or into the venous blood line leaving the hemofilter.

In addition to the removal of metabolic products, one of the most important problems of every kidney replacement therapy, such as hemodialysis, hemofiltration and peritoneal dialysis, lies in the correction of metabolic acidosis. For this reason, the dialysis solutions used in each of these processes contain a buffer.

Three common buffers often used in dialysis solutions are bicarbonate, lactate, and acetate. While initially bicarbonate was the primary buffer used in dialysis solutions, over time lactate and acetate were used as substitutes for bicarbonate. This was due to the difficulty in preparation and storage of bicarbonate-buffered dialysis solutions. Lactate and acetate buffers were found to provide greater stability in use over the previous bicarbonate-buffered solutions. See U.S. Pat. No. 5,211,643.

However, since bicarbonate ions provide advantages over acetate or lactate ions, bicarbonate is again surfacing as the primary buffer used in dialysis solutions. Tests have been conducted that indicate patients exhibit a better tolerance for bicarbonate dialysis solutions. In patients with a multiple organ failure, bicarbonate-buffered solutions are preferred because of the lack of metabolic interference. Further, certain treatments require sterile dialysis solutions containing bicarbonate, calcium and magnesium.

For example, one may have to dialyze a uremic patient who has developed hypotension and lactate acidosis. In such a patient, the lactate or acetate in conventional dialysates may not be metabolized to bicarbonate because of tissue hypoxia, and acidosis may be further worsened because bicarbonate is removed during dialysis. Using bicarbonate-containing dialysates in such a patient will add bicarbonate to the blood and also remove lactate. For these reasons, some researchers have recommended bicarbonate-buffered dialysis as adjunctive treatment for severe lactate acidosis. T. S. Ing. et al, *Bicarbonate-buffered peritoneal dialysis*, The International Journal of Artificial Organs, Volume 8, No. 3, p. 121–124 (1985).

Another potential application of bicarbonate-buffered solutions may be for patients who experience abdominal pain or discomfort when conventional acetate- or lactate-buffered dialysates are infused. The abdominal pain may be related to the unphysiologically high acidity of acetate- and lactate-buffered dialysates. Conceivably, bicarbonate-buffered dialysate, with its more physiologic pH, might decrease the incidence of such symptoms. Id.

The use of medical bicarbonate solutions for injection or for dialysis treatment is known. However, due to the difficulty in preparation and storage of these solutions, a vast array of literature is dedicated to attempts to remedy the stability problem of bicarbonate solutions. Three main problems need to be addressed when manufacturing and storing medical bicarbonate solutions.

First, in solution, bicarbonate is in equilibrium with $CO_2$ gas, which easily escapes from the solution. As a result, carbonate, a potential irritant, may form, and the pH of the solution is thereby increased. To avoid these phenomena from occurring, the bicarbonate can be stored in a powder form until just before use as described in U.S. Pat. No. 4,489,535 and Jonsson et al, European Patent Application 0 278 100 for machine-controlled dialysis.

Alternatively, an impermeable gas barrier can be used to protect the solution. Or, for hemodialysis, the $CO_2$ content of the solution can be controlled as described in Murphy et al, *Use of An Artificial Kidney*, J Lab. Clin. Med., Volume 40, pp. 436–444 (1952). U.S. Pat. No. 4,584,176 and European Patent No. 0 209 607 describe controlling the $CO_2$ content of a bicarbonate-based solution. Moreover, the addition of buffers, such as glycylglycine, has been proposed to further stabilize the bicarbonate solution. See U.S. Pat. No. 4,959,175.

Still further, another approach focuses on generating carbon dioxide within a container to stabilize bicarbonate solutions. See U.S. Pat. No. 5,383,324. In the '324 patent, a device can be used to generate and maintain carbon dioxide pressure within a container. The device can either be positioned within a container that houses the bicarbonate solution or within an overpouch that surrounds the container filled with the bicarbonate solution. The device can be used before, during or after steam sterilization.

Second, bicarbonate solutions for injection and for dialysis generally contain calcium and/or magnesium ions. In the presence of bicarbonate, these ions form calcium carbonate and magnesium carbonate, respectively, which at increased pHs typically precipitate from the solution. To initially remedy this problem, bicarbonate solutions are often made from concentrates, ranging from slightly concentrated, two-fold or less, to much more concentrated solutions. Bicarbonate on the one hand and calcium and/or magnesium on the other hand are included in separate concentrates. These concentrates are then mixed to obtain a ready-to-use solution. Alternatively, the concentrates are mixed and diluted or diluted and mixed.

In order to avoid the precipitation of carbonate salts, some have suggested the bicarbonate concentrate should be acidified when manufactured. See U.S. Pat. No. 5,211,643. Specifically, the '643 patent proposes adjusting the pH value of the bicarbonate concentrate to less than 7.6 by addition of a physiologically tolerable acid.

Alternatively, others have proposed to leave the pH of the bicarbonate concentrate unadjusted. See U.S. Pat. No. 4,489,535. Left unadjusted, the pH of the bicarbonate concentrate is about 8.0–8.4. The Merck Index, $12^{th}$ Ed., Merck Research Laboratories, Whitehouse Station, N.J., p. 1472 (1996); Boen S T, A clinical study of factors governing its effectiveness, *Peritoneal Dialysis*, p. 76, Van Gorcum & Comp, Assen, The Netherlands (1959); Odel H M et al., Peritoneal lavage as an effective means of extrarenal excretion. A clinical appraisal, *American Journal of Medicine*, 9, 63–77 (1950). The unadjusted bicarbonate concentrate is then mixed with an acid or acidified concentrate, either before or after dilution if dilution is needed. Acidification has been achieved with organic acids (acetic acid, lactic acid), inorganic acids (hydrochloric acid) or with carbon dioxide. Ing. et al, *Bicarbonate-buffered peritoneal dialysis*, Volume 8, No. 3, p. 121–124 (1985).

The problem with both of these approaches is that the bicarbonate based solution needs a gas barrier, either as a primary container or as an overwrap. In case of accidental damage to the gas barrier, the bicarbonate concentrate will lose carbon dioxide, and the pH will increase. Upon mixing of the acid concentrate with the bicarbonate concentrate, the pH of the bicarbonate concentrate will no longer match with the pH of the acid concentrate. The mixed solution will no longer be in the physiologic range, and a calcium carbonate precipitate will form immediately upon mixing.

To avoid gas barrier damage, thick containers have been used instead of flexible containers. However, these do not collapse upon draining and therefore need to be vented for use in peritoneal dialysis or hemofiltration. This has the inherent risk of infection.

U.S. Pat. No. 5,296,242 to Zander describes the use of a stable aqueous solution in the form of two separately stored single solutions, one containing a metabolizable organic acid, the other alkali bicarbonate and alkali carbonate. The '242 patent relates to adjusting the pH of the dextrose compartment with an organic acid; the dextrose compartment is adjusted to a pH range of 4.0 to 6.0. Not only do the inventors believe a physiological solution will not be achieved with such a high pH for the dextrose component, problems arise from the use of organic acids. For example, in patients with liver failure, the body has difficulty in metabolizing organic acids, and it is therefore preferable to have all buffer available as bicarbonate. In case of peritoneal dialysis, the presence of organic acids and dextrose in the same container will enhance the formation of glucose degradation products, which in turn may damage the peritoneal membrane.

Third, bicarbonate solutions for injection and for certain types of dialysis need to be sterile. Sterile filtration, steam sterilization, radiation or another suitable sterilization method may be used. When steam sterilization is used, many substances cannot be autoclaved together with bicarbonate. Therefore, the solution must be sterilized in at least two parts: one part containing the bicarbonate; and another part containing the incompatible substances(s), such as dextrose. In practice, two containers can be used, or alternatively, multi-compartment containers can be used. See U.S. Pat. Nos. 4,396,383 and 4,465,488.

In light of the problems associated with bicarbonate-based solutions, bicarbonate solutions for peritoneal dialysis are typically either prepared in the hospital just before use or are stored in a two-chamber container made of a steam-sterilizable gas barrier material. Of course, preparing the bicarbonate solution in the hospital is time-consuming and poses sterility problems. On the other hand, the steam-sterilizable gas barrier materials are expensive and the barrier may be accidentally lost due to damage during production and/or transportation.

Therefore, a need still exists for an improved way to manufacture and store bicarbonate-based solutions.

SUMMARY OF THE INVENTION

The present invention provides devices and methods for stabilizing bicarbonate-based peritoneal dialysis solutions. Specifically, the present invention relates to a new way to formulate a bicarbonate-based solution for peritoneal dialysis or hemofiltration. The solution of the present invention is formulated and stored in at least two parts—an alkaline bicarbonate concentrate and an acidic concentrate. The invention focuses on the adjustment of the chemical parameters and the pH levels of the concentrates, so that upon mixing, the two concentrates always provide a solution with an acceptable pH in the physiologic range. The invention surprisingly avoids the need for carbon dioxide addition to the bicarbonate solution as well as the use of an expensive gas barrier material, which were used previously to maintain the stability of a bicarbonate-based solution. Also, it does not require the use of organic acids or other undesired substances.

The present invention provides a two-part bicarbonate containing solution. The first part of the solution is housed in a first container. The first part includes an alkaline bicarbonate concentrate whose pH is adjusted to about 8.6 to 10.0. The second part of the solution is housed in a second container. The second part includes an acidic concentrate having a pH effective to obtain, when the first part and the second part are mixed together, a mixed solution having a pH ranging from about 6.5 to 7.6. The pH of the acidic concentrate preferably ranges from about 1.0 to 3.0. In a preferred embodiment, the first and second containers are two chambers of a multi-chamber container.

The pH of the alkaline bicarbonate is chemically adjusted upwards at the time of manufacture to more alkaline values. Initially, when prepared, the bicarbonate concentrate has a pH of 8.0–8.4. Chemically increasing the pH of the bicarbonate component upwards is indeed counter intuitive as the desired pH range for the mixed solution is 6.5 to 7.6 (close to the pH of blood) which is well below the pH of a freshly made bicarbonate solution. Further, container interactions generally increase at more extreme pH values. Nevertheless, the inventors found that adjusting of the bicarbonate component to these alkaline pH values, combined with a dextrose component at a low pH yields a stable product that does not need a gas barrier.

In one embodiment, the pH of the bicarbonate-based concentrate is chemically adjusted to about 8.6, and allowed to adjust further over time during storage. The inherent instability of the concentrate effectively increases the pH with time and storage due to carbon dioxide loss until it reaches a steady state level of about 9 to 10. The pH naturally rises during storage when the solution is housed in a gas permeable container. However, the initial adjustment allows to obtain a pH in a physiological range (6.5–7.6) after mixing.

Alternatively, the alkaline bicarbonate concentrate is adjusted by adding a physiologically acceptable base to the aqueous solution containing sodium bicarbonate having an original pH of about 8.0–8.4 to increase the pH thereof to a pH of about 9.0 to 10.0.

The inventors have found that when the bicarbonate concentrate is either formulated or naturally allowed to obtain a pH of about 9.0 to 10.0, the pH of the bicarbonate-based concentrate is in a steady state and is in equilibrium with the ambient air. With a bicarbonate concentrate starting at about pH 8.6, although there is some variation in the pH of the mixed bicarbonate solution, the inventors have discovered that with the appropriate selection of the parameters of the concentrates, particularly the pH of the dextrose concentrate, the pH of the mixed solution is always within an acceptable physiological pH range (6.5–7.6). The invention again focuses on the adjustment of the chemical parameters and the pH levels of the concentrates.

In a preferred embodiment, the present invention provides a multi-chamber container for storing a bicarbonate-based solution for peritoneal dialysis or hemofiltration. The container includes a first chamber housing an alkaline bicarbonate concentrate. The alkaline bicarbonate concentrate is adjusted to have a pH in a range of about 8.6 to 10.0. The second chamber of the multi-chamber container houses an acidic concentrate. The acidic concentrate has a pH of about 1.0–3.0, so that, when the alkaline bicarbonate concentrate is mixed with the acidic concentrate, a mixed solution having a pH in a physiologic range of about 6.5 to 7.6 is obtained. In a preferred embodiment, the acidic concentrate has a pH of about 1.3 to 2.5.

The present invention also provides a method for stabilizing bicarbonate solutions. The method includes the step of housing an alkaline bicarbonate concentrate in a first container and housing an acidic concentrate in a second container. The pH of the alkaline bicarbonate concentrate is adjusted to a range of about 8.6 to 10.0. Further, the acidic concentrate is adjusted to a pH effective to obtain, when the alkaline bicarbonate concentrate is mixed with the acidic concentrate, a mixed solution having a pH ranging from about 6.5 to 7.6. Preferably, the acidic concentrate has a pH ranging from about 1.0 to 3.0.

An advantage of the present invention is that it provides new apparatuses and methods for formulating a bicarbonate-based peritoneal dialysis solution.

Another advantage of the present invention is that it avoids the use of an expensive gas barrier material to maintain the stability of bicarbonate-based solutions. Such steam sterilizable gas barrier materials are expensive, rarely fail proof and are not required when using the present invention. The invention therefore solves the problem of maintaining the physical integrity of the gas barrier materials during manufacturing and storage. Consequently, the invention allows for the production of sterile bicarbonate-based peritoneal dialysis solutions in a manufacturing plant at very low cost and to ship a chemically stable product to the hospital or a patient's home.

Yet another advantage of the present invention is that it ensures that the bicarbonate solution can be stored for long periods of time, while it makes a gas barrier redundant. The two-part solution is stable for more than six months.

Moreover, an advantage of the present invention is that a ready-to-use bicarbonate-based solution with a physiologic pH range can be obtained without using expensive gas barrier materials.

Additional features and advantages of the present invention are described in, and will be apparent from, the detailed description of the presently preferred embodiments as well as the drawings.

BRIEF DESCRIPTION OF THE DRAWINGS

FIGS. 3 and 4 graphically illustrate the respective pH levels of bicarbonate concentrates, acidic concentrates and mixed solutions for testing conducted in Experiment No. 5.

DETAILED DESCRIPTION OF THE PRESENTLY PREFERRED EMBODIMENTS

The present invention provides both apparatuses and methods for stabilizing bicarbonate-based solutions. The solutions are formulated and stored in at least two parts—an alkaline bicarbonate concentrate and an acidic concentrate. The two parts are housed in two separate containers. The bicarbonate concentrate is adjusted to have a pH ranging from about 8.6 to 10.0. Whereas, the acidic concentrate is formulated at a stable, acidic pH, so that upon mixing of both concentrates, a mixed solution with a pH in a narrow physiologic range is obtained. The acidic concentrate has a pH ranging from about 1.0 to 3.0. The mixed solution is prepared by mixing the concentrates just before use.

The two part bicarbonate-containing solution of the present invention are formulated and stored separately, and then are mixed just prior to use. A variety of containers can be used to house the two parts of the bicarbonate-containing solution, such as separate containers (i.e. flasks or bags) that are connected by a suitable fluid communication means. Preferably, a multi-chamber container is used to house the two concentrates.

Figure 1:
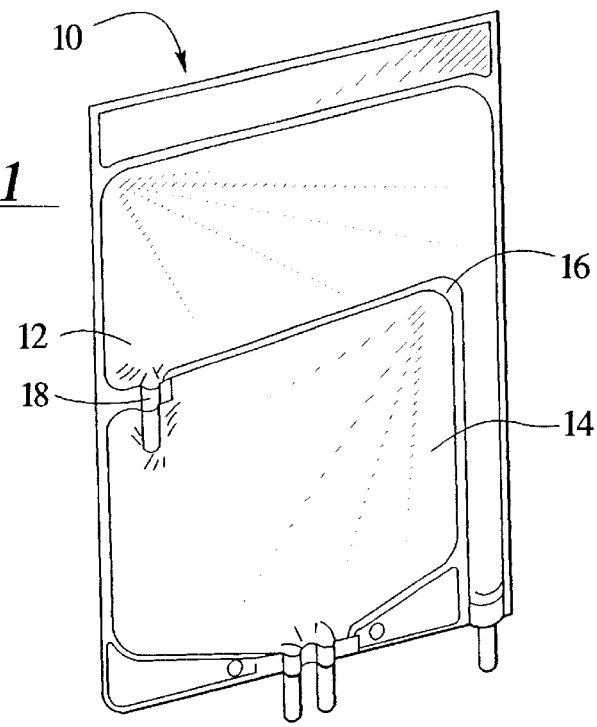
FIG. 1 illustrates a multi-chamber bag for storing a two-part bicarbonate solution made pursuant to the present invention.

FIG. 1 illustrates a suitable container for storing a bicarbonate-based solution. The multi-chamber 10 has a first chamber 12 and a second chamber 14. The interior of the container is divided by a heat seal 16 into the two chambers. The multi-chamber container 10 also has a frangible connector 18 between the first chamber 12 and the second chamber 14. To mix the solution within the chambers 12 and 14, the frangible connector 18 is broken. The transfer of product is thereby initiated from the first chamber 12 to the second chamber 14. The multi-chamber 10 houses at least two non-compatible solutions that after mixture will result in a ready-to-use dialysis solution. An example of the multi-chambered container 10 is set forth in U.S. Pat. No. 5,431,496, the disclosure of which is incorporated herein by reference. The container 10 can be made from a gas permeable material, such as polypropylene. Alternatively, both containers can be separated by a peel seal, which is broken before use by the patient.

Although the multi-chamber container disclosed herein is designed to be used for any medical procedure requiring bicarbonate, the embodiment illustrated in FIG. 1 is conveniently used for peritoneal dialysis and hemofiltration. To this end, in an embodiment, the first chamber 12 contains a dextrose concentrate, whereas the second chamber contains a bicarbonate concentrate. In a preferred embodiment, the first chamber 12 further includes calcium chloride, magnesium chloride and a physiologically tolerable acid to adjust the pH of the acidic concentrate. The second chamber 14 can further include sodium chloride and lactate. In an embodiment, the bicarbonate concentrate also includes a physiologically tolerable base to adjust the pH of bicarbonate concentrate within the desired range.

The bicarbonate-based concentrate is adjusted upwards to have a pH ranging from about 8.6 to 10.0. The pH of the bicarbonate concentrate can be adjusted in two ways. The pH of the bicarbonate-based concentrate can be chemically adjusted to 8.6, and allowed to adjust further over time during storage The inherent instability of the concentrate effectively increases the pH with time and storage due to carbon dioxide loss until it reaches a steady state level of about 9 to 10. The pH naturally rises during storage when the solution is housed in a gas permeable container. However, the initial adjustment allows one to obtain a pH in a physiological range (6.5–7.6) after mixing. Alternatively, the alkaline bicarbonate concentrate is adjusted by adding a physiologically acceptable base to the aqueous solution containing sodium bicarbonate to increase the pH thereof to a pH of about 9.0 to 10.0.

The bicarbonate concentrate is stable for long periods of time without the use of either a gas barrier material or the addition of carbon dioxide. The inventors have found that the concentrates are stable for over 6 months.

In accordance with the present invention, the bicarbonate concentrate contains sodium bicarbonate, sodium chloride and sodium lactate. In an embodiment, the bicarbonate concentrate also includes a physiologically acceptable base to adjust the pH of the bicarbonate concentrate to the desired alkaline range. Any strong base that is physiologically acceptable for the patient's treatment can be used to adjust the pH of the bicarbonate concentrate. Suitable bases that can be used include, for example, sodium hydroxide, potassium hydroxide, calcium hydroxide, and magnesium hydroxide.

In order to achieve a physiological pH for the mixed bicarbonate solution, the dextrose concentrate is formulated at a stable, acidic pH. The pH of the acidic concentrate is chosen, so that upon mixing of both concentrates, a mixed solution with a pH in a physiologic range is obtained. Preferably, the mixed solution has a pH ranging from about 6.5 to 7.6 at 25° C. The inventors have determined that when an acidic concentrate having a pH of about 1.0 to 3.0 is combined with the bicarbonate concentrate, a physiological pH is obtained for the mixed solution. In a preferred embodiment, the pH of the acidic concentrate ranges from about 1.3 to 2.5.

The acidic concentrate preferably contains dextrose, calcium chloride, magnesium chloride and a physiologically tolerable acid to adjust the pH of the acidic concentrate. A variety of strong inorganic acids can be used to adjust the acidic concentrate to the appropriate pH. Suitable acids that can be used, for example, hydrochloric acid, sulphuric acid, nitric acid, hydrogen bromide and hydrogen iodide.

The bicarbonate concentrate and the dextrose concentrate are mixed together to form a ready-to-use solution for peritoneal dialysis or hemofiltration. Preferably, the two concentrates are mixed in a ratio ranging from 1:50 to 50:1 (volume:volume); more preferably, the two concentrates are mixed in a 1:1 to 1:3 (volume:volume) ratio. In an embodiment, the subsequent dialysis solution contains the following ingredients in the identified amount: bicarbonate (5 to 45 mM); calcium (0.2 to 2.0 mM); sodium (100 to 150 mM); magnesium (0 to 1.5 mM); potassium (0 to 4.5 mM); chloride (70 to 120 mM); lactate (0 to 60 mM); and acetate (0 to 60 mM). The dialysis solutions have a physiologically acceptable pH ranging from about 6.5 to 7.6.

Pursuant to the present invention, any osmotic agent can be used in the solution. The peritoneal dialysis solution includes an osmotic agent in an amount of 0.1 to 20 weight percent. Preferably, suitable osmotic agents are glucose, glucose polymers, modified starch, amino acids, peptides, and glycerol.

The inventors have identified that with the appropriate selection of the parameters of the concentrates, a two-part bicarbonate-based solution can be stored for long periods of time and can be stored in a gas permeable container. The invention thus relies on the adjustment of the chemical parameters and the pH levels of the concentrates. The adjustments are made, so that upon mixing, the two concentrates always provide a solution with an acceptable physiological pH range.

By way of example, and not limitation, experimental testing conducted to demonstrate the effectiveness of the present invention will now be set forth.

EXPERIMENT NO. 1: pH OF THE ALKALINE CONCENTRATE

This experiment was conducted to evaluate the evolution of pH levels of bicarbonate concentrates stored in gas permeable containers. If bicarbonate based solutions are not protected by a gas barrier material, the pH level increases during storage. With this experiment, the inventors determined that while the pH levels do increase, they reach a maximum pH level.

Figure 2:
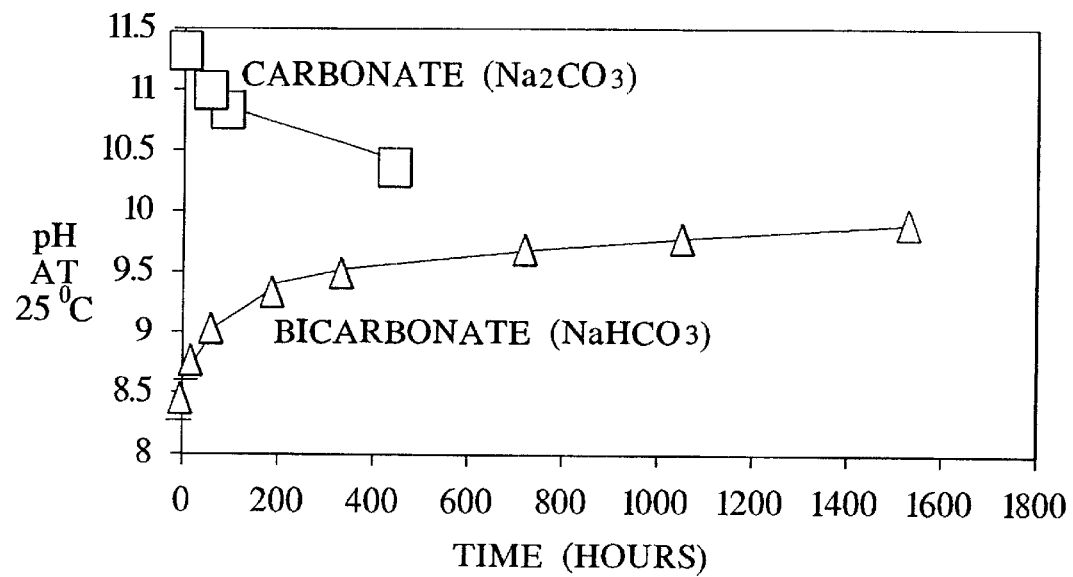
FIG. 2 graphically illustrates the pH level shift of bicarbonate solutions tested in Experiment No. 1.

FIG. 2 presents pH levels over time of a 50 mM bicarbonate concentrate, stored in gas permeable containers. With time, a maximum pH of about 9–10 is reached. Likewise, if a 50 mM carbonate concentrate, with a pH of 11 is stored in a gas permeable container, pH decreases over time to the same values.

EXPERIMENT NO. 2: MIXED SOLUTION WITH PHYSIOLOGIC pH

Based on the range between the original and ending pH of the bicarbonate concentrate from Experiment 1, the inventors have determined they can formulate stable, acidic concentrates that will, when mixed with the bicarbonate concentrate, produce mixed solutions with physiological pH levels. This experiment demonstrates that when a bicarbonate concentrate with a pH of about 8.6–10.0 is mixed with a dextrose concentrate at a pH of about 1.3–2.5, a mixed solution with a physiological pH level of 6.5–7.6 is obtained.

The tested bicarbonate and dextrose concentrates and the mixed solution had the composition detailed in Table 1.

TABLE 1

Composition of solutions

| DEXTROSE concentrate | |
|---|---|
| Dextrose.H2O | 84.94 g/l |
| CaCl2.2H2 | 0.369 g/l |
| MgCl2.6H2 | 0.102 g/l |
| HCl (adj.) | 21.2 mEq/l |

TABLE 1-continued

Composition of solutions

BICARBONATE concentrate

| | |
|---|---|
| NaCl | 9.51 g/l |
| Na Lactate | 3.36 g/l |
| NaHCO3 | 4.68 g/l |
| NaOH (adj) | 15.6 mEq/l |

MIXED SOLUTION

| | |
|---|---|
| Dextrose.H2O | 42.5 g/l |
| Calcium | 1.25 mM |
| Magnesium | 0.25 mM |
| Chloride | 95 mM |
| Sodium | 132 mM |
| Lactate | 15 mM |
| Bicarbonate | 25 mM |

The concentrates were stored separately, and the final tested solutions were obtained after mixing the concentrates in a 1:1 (volume:volume) ratio.

Table 2 sets forth the pH levels of the bicarbonate and dextrose concentrates as well as the final solutions tested in this experiment.

TABLE 2 pH of final bicarbonate/dextrose solution

| pH of bicarbonate concentrate | 8.6 | 8.6 | 8.8 | 8.9 | 9.1 | 9.3 | 9.5 | 10.0 | 10.0 |
|---|---|---|---|---|---|---|---|---|---|
| pH of dextrose concentrate | 1.7 | 2.5 | 1.7 | 1.7 | 1.7 | 1.7 | 1.7 | 1.3 | 1.5 |
| pH of final mixed solution | 6.5 | 7.6 | 6.6 | 6.7 | 6.8 | 7.1 | 7.4 | 6.5 | 7.6 |

EXPERIMENT NO. 3: SOLUTION FOR MEDICAL USE

This experiment demonstrates that when a bicarbonate concentrate with a pH of about 9.5 is mixed with a dextrose concentrate at about pH 1.7, not only a mixed solution with a physiological pH level of about 7.3 is obtained, but the solution is suitable for medical use and free from particulate material or calcium carbonate precipitate.

The nominal composition of the dextrose concentrate and the bicarbonate concentrate are listed in Tables 3 and 4 below.

TABLE 3

Sterile Dextrose Concentrate

COMPOSITION

| | |
|---|---|
| Glucose.H$_2$O | 85.00 g/l |
| CaCl$_2$.2H$_2$O | 0.368 g/l |
| MgCl$_2$.6H$_2$O | 0.102 g/l |
| pH (at ambient conditions) | 1.7* |

*the pH of the solution was adjusted using HCl.

TABLE 4

Sterile Bicarbonate Concentrate

COMPOSITION

| | |
|---|---|
| Sodium chloride | 10 76 g/l |
| L-Sodium lactate | 3.36 g/l |
| Sodium bicarbonate | 4.20 g/l |
| pH (at ambient conditions) | pH = 9.5* |

*the pH of the solution was adjusted using NaOH.

The two concentrates were mixed in a 1:1 (volume: volume) ratio and analyzed. The mixed solution was then centrifuged for 5 minutes at 4000G to remove any precipitating material and analyzed again. The results from this experiment are detailed in Table 5 below.

TABLE 5

Results

| | Dextrose concentrate | Bicarbonate concentrate | Mixed solution (immediately after mixing) | Mixed solution (after centrifugation) |
|---|---|---|---|---|
| pH (at ambient temperature) | 1.7 | 9.5 | 7.3 | 7.6 |
| Calcium choride.2H2O (g/L) | 0.361 | 0 | 0.182 | 0.184 |
| Particles greater than 10μ (/mL)* | 3 | 6 | 19 | 0 |
| Particles greater than 25μ (/mL)* | 0 | 2 | 0 | 0 |

*Pharmacopea limit: not more than 25 particles/mL greater than 10μ and not more than 3 particles/mL greater than 25μ

Table 5 demonstrates that after centrifugation of the mixed solution, the calcium chloride content is maintained, showing the absence of calcium precipitation upon mixing.

EXPERIMENT NO. 4

This experiment was conducted to further evaluate whether a precipitate of calcium carbonate would form when bicarbonate and dextrose solutions, which were adjusted to various pH levels, were mixed at a 1:1 ratio. Analyses performed in this experiment included visual inspection, pH determination, instrumental particle counting, microscopic assay for particulate matter per USP 23<788>, calcium determination by Inductively Coupled Plasma-Atomic Emission Spectroscopy ("ICP-AES"), and an examination of isolated particulate matter via scanning electron microscopy with energy dispersive x-ray spectrometry ("SEM/EDXS").

Test Solutions

The following test solutions were prepared:

Solution A (Bicarbonate Concentrate pH 9.5)-9.5 g/l Sodium Chloride, 3.36 g/l Sodium Lactate (or 5.6 g/l of 60% purity), 4.68 g/l Sodium Bicarbonate, pH adjusted with 1N NaOH to 9.5.

Solution B (Dextrose Concentrate pH 1.6–1.7)-84.9 g/l of Dextrose Hydrous (or 77.2 g/l Anhydrous), 0.368 g/l Calcium Chloride dihydrate, 0.102 g/l Magnesium Chloride Hexahydrate, pH Adjusted with HCl to about 1.65.

Solution C (Dextrose Concentrate pH 5.5–6.0)-84.9 g/l of Dextrose Hydrous (or 77.2 g/l Anhydrous), 0.368 g/l Calcium Chloride dihydrate, 0.102 g/l Magnesium Chloride Hexahydrate.

Solution D (Carbonate Concentrate pH 11.0)-9.5 g/l Sodium Chloride, 3.36 g/l Sodium Lactate (or 5.6 g/l of 60% purity), 5.83 g/l Sodium Carbonate.

For each of the test solutions, the volume of the mixed reagents was brought to 2 liters with Nanopure water in a volumetric flask. Then, a final pH measurement was taken, which is identified below for each solution, and the resulting solution was recirculated through a 0.40 micron retention rated filter prior to any mixing or analysis.

Test Articles

Test articles were prepared by combining 100 mL volumes of the test solutions together in a glass container. The dextrose solution was added to a glass container first followed by addition of the bicarbonate solution. The solutions were then inverted 20 times to enure complete mixing. The test mixtures were kept at ambient conditions and all testing was performed on the same day of mixing. Table 6 below sets forth the various test articles.

TABLE 6

| Test Article | Bicarbonate or Carbonate | Dextrose Concentrate |
|---|---|---|
| AB | pH 9.5 (A) | pH~1.65 (B) |
| AC | pH 9.5 (A) | pH 5.5–6.0 (C) |
| CD | pH 11.0 (D) | pH 5.5–6.0 (C) |

ANALYSIS OF TEST SOLUTIONS AND TEST ARTICLES

A variety of tests were conducted on each test solution and test article. Specifically, each test solution and test article was analyzed by visual inspection, pH determination, instrumental particle counting, USP microscopic assay for particulate matter, calcium determination by ICP-AES, and an examination of isolated particulate matter via SEM/EDXS. The test articles were evaluated prior to and after filtration through a 0.45 micron polycarbonate filter. The results of the analyses performed on the test solutions and article, are set forth in Table 7 below.

meration for both the microscopic evaluation and instrumental particle counting were well below the limits. The results of the ICP-AES analysis show that the calcium concentration in the mixed solution was about half of the concentration in the dextrose concentrate, either before or after filtration. Given the 1:1 mixing, this indicates that no calcium precipitated. In addition, the test article was filtered on polycarbonate filters and examination of the filters for the presence of calcium carbonate by SEM/EDXS was also negative. Thus, based on the assays performed, no calcium carbonate precipitate was detected in the test article made pursuant to the present invention, which was obtained by mixing a bicarbonate concentrate at about pH 9.5 and a dextrose concentrate containing calcium and magnesium at about pH 1.65.

In contrast, calcium carbonate precipitation did form in the comparative test articles, namely test article AC and test article DC. In these test articles, a bicarbonate solution adjusted to a pH of 9.5 (test article AC) or a carbonate solution having a pH of 11.0 (test article DC) were mixed with a dextrose concentrate having a pH of 5.5 to 6.0. All particle enumeration results for both of the test articles were above acceptable limits and a calcium carbonate precipitate was identified.

EXPERIMENT NO. 5: LONG TERM STORAGE

This experiment demonstrates that when a bicarbonate and dextrose concentrate, made according to the present invention, are stored for 6 months, a mixed solution with a pH in the physiological range of 6.5–7.6 is obtained over the entire period studied.

Embodiment 1. A bicarbonate-based concentrate with a pH of 8.6 was prepared. pH was allowed to adjust further over time during storage. However, the initial adjustment allows one to obtain a pH in a physiological range (6.5–7.6) after mixing.

The container was presented as a two-chambered bag with a peel seal separating the chambers. The pH of the bicar-

TABLE 7

| Sample ID | pH | Visual inspection for crystalline precipitate | USP Microscopic Analysis (particles/mL) | | Instrumental Particle Counting (particles/m/L) | | Calcium Concentration (g/l) | Presence of calcium carbonate by SEM/EDXS |
|---|---|---|---|---|---|---|---|---|
| | | | ≥10 μm | ≥25 μm | ≥10 μm | ≥25 μm | | |
| USP Limits | | Absent | 12 | 2 | 25 | 3 | | |
| Test Solution A | 9.5 | Absent | 0.4 | 0.0 | 0.7 | 0.1 | 0.001 | Negative |
| Test Solution B | 1.6 | Absent | 0.0 | 0.0 | 0.2 | 0.0 | 0.356 | Negative |
| Test Solution C | 5.7 | Absent | 0.3 | 0.0 | 0.3 | 0.0 | 0.351 | Negative |
| Test Solution D | 11.0 | Absent | 0.3 | 0.0 | 0.3 | 0.1 | 0.001 | Negative |
| AB Mixed, Pre-Filtration | 7.1 | Absent | 0.1 | 0.0 | 6.5 | 0.5 | 0.167 | Negative |
| AB Mixed, post-Filtration | 7.5 | Absent | 0.0 | 0.0 | 4.4 | 0.4 | 0.177 | Negative |
| AC Mixed, Pre-Filtration | 9.5 | Small white particles | TNTC | TNTC[1] | 800.3 | 27.0 | 0.132 | Positive |
| AC Mixed, Post-Filtration | 9.5 | Absent | TNTC | TNTC | 1230.7 | 0.0 | 0.094 | Positive |
| CD Mixed, Pre-Filtration | 10.6 | Small white particles | TNTC | TNTC | 209.2 | 5.1 | 0.119 | Positive |
| CD Mixed, Post-Filtration | 10.5 | Small white particles | 2.1 | 0.4 | 833.8 | 7.5 | 0.087 | Positive |

[1]TNTC: Too numerous to count.

These test results demonstrate the absence of the formation of a calcium carbonate precipitate for the test article (AB Mixed) made in accordance with the present invention. The visual inspection results indicate that no crystalline precipitate was detected. The results of the particle enubonate and dextrose containing solutions were matched in order to obtain a physiological pH after mixing (1:1 volume ratio). The tested sterile dextrose and bicarbonate concentrates had the compositions and pH adjustments detailed in Tables 8 and 9, respectively.

TABLE 8

Sterile Dextrose Concentrate

| COMPOSITION | | |
|---|---|---|
| Glucose.H$_2$O | g/l | 85.00 |
| CaCl$_2$.2H$_2$O | g/l | 0.368 |
| MgCl$_2$.6H$_2$O | g/l | 0.102 |
| pH at ambient conditions | | 2.0* |

*the pH of the solution was adjusted using HCl.

TABLE 9

Sterile Bicarbonate Concentrate

| COMPOSITION | | |
|---|---|---|
| Sodium chloride | g/l | 10.76 |
| L-Sodium lactate | g/l | 3.36 |
| Sodium bicarbonate | g/l | 4.20 |
| pH adjusted to (at ambient conditions) | | 8.6 |

The sterile containers were stored under controlled conditions at 25° C. and 40° C.- 60% relative humidity. Periodically, the bicarbonate and the dextrose concentrates were evaluated. The mixed solution obtained by manual mixing of equal volumes of dextrose and bicarbonate solution (ratio 1:1) was also evaluated.

The following observations were obtained after storage of the containers for six months. Table 10 sets forth the respective pH levels at the defined time of storage. And, FIG. 3 presents the pH levels of the different alternatives during 6 months of storage at 25° C.

TABLE 10

| Period (month) | Bicarbonate | Mixed solution | Dextrose |
|---|---|---|---|
| 0 | 8.6 | 7.1 | 2.0 |
| 1 | 8.7 | 7.1 | 2.0 |
| 3 | 8.9 | 7.3 | 2.0 |
| 6 | 9.1 | 7.3 | 2.0 |

As expected, the pH level of the bicarbonate concentrate in Embodiment No. 1 is moving with time and storage. After mixing the bicarbonate concentrates of Embodiment 1 with the matching dextrose concentrate, a physiological pH level is obtained during the entire period studied.

Embodiment 2. The pH of the bicarbonate concentrate was adjusted to about 9.5 by adding sodium hydroxide. After mixing with the acidified dextrose solution, a mixed solution with a physiological pH is obtained over the entire study period of 6 months.

The container was presented as a two-chambered bag with a peel seal separating the chambers. The pH of the bicarbonate and dextrose containing solutions were matched in order to obtain a physiological pH after mixing (1:1 volume ratio). The tested sterile dextrose and bicarbonate concentrates had the compositions and pH adjustments detailed in Tables 11 and 12, respectively.

TABLE 11

Sterile Dextrose Concentrate

| COMPOSITION | | |
|---|---|---|
| Glucose.H$_2$O | | 85.00 g/l |
| CaCl$_2$.2H$_2$O | | 0.368 g/l |
| MgCl$_2$.6H$_2$O | | 0.102 g/l |
| pH at ambient conditions | | 1.7* |

*the pH of the solution was adjusted using HCl.

TABLE 12

Sterile Bicarbonate Concentrate

| COMPOSITION | | |
|---|---|---|
| Sodium chloride | g/l | 10.76 |
| L-Sodium lactate | g/l | 3.36 |
| Sodium bicarbonate | g/l | 4.20 |
| pH (at ambient conditions) | | pH = 9.5* |

*the pH of the solution was adjusted using NaOH.

The tested sterile containers were stored under controlled conditions at 25° C. and 40° C.- 60% relative humidity. Periodically, the bicarbonate and the dextrose concentrates were evaluated. The mixed solution obtained by manual mixing of equal volumes of dextrose and bicarbonate solution (ratio 1:1) was also evaluated. Table 13 sets forth the respective pH levels for Embodiment 2 at the defined time of storage.

TABLE 13

| Period (month) | Bicarbonate | Mixed solution | Dextrose |
|---|---|---|---|
| 0 | 9.5 | 7.3 | 1.7 |
| 1 | 9.5 | 7.4 | 1.7 |
| 3 | 9.5 | 7.4 | 1.7 |
| 6 | 9.5 | 7.2 | 1.7 |

FIG. 4 demonstrates that the pH level of the bicarbonate concentrate of Embodiment No. 2 is maintained at 9.5 after sterilization and after 6 months of storage. After mixing the bicarbonate concentrates of alternative 2 with the matching dextrose concentrate, a physiological pH level is obtained.

Overall, the results demonstrate the feasibility of manufacturing and storing the bicarbonate-based solution of the present invention in a plastic material. The bicarbonate-based solution can be prepared in a plastic material, without a carbon dioxide gas barrier, provided that the concentrates are adequately adjusted (pH levels, levels of ingredients).

Examples of suitable formulations for peritoneal dialysis solutions are given above. By way of example, and not limitation, the following formulations are given for a substitution fluid for continuous renal replacement therapy.

| Component | Formulation 1 | Formulation 2 |
|---|---|---|
| Compartment 1 | | |
| Ca++ | 3 mmol/l | 3 mmol/l |
| Mg++ | 1 mmol/l | 1 mmol/l |
| Cl– | 8 mmol/l | 8 mmol/l |
| Glucose (g/l) | 2 g/l | 0 |

-continued

| Component | Formulation 1 | Formulation 2 |
|---|---|---|
| Compartment 2 | | |
| Na+ | 280 mmol/l | 280 mmol/l |
| K+ | 0 | 4 mmol/l |
| Cl− | 230 mmol/l | 204 mmol/l |
| HCO3− | 50 mmol/l | 80 mmol/l |
| Mixed solution (1:1) | | |
| Na+ | 140 mmol/l | 140 mmol/l |
| K+ | 0 | 2 mmol/l |
| Ca++ | 1.5 mmol/l | 1.5 mmol/l |
| Mg++ | 0.5 mmol/l | 0.5 mmol/l |
| Cl− | 119 mmol/l | 106 mmol/l |
| HCO3− | 25 mmol/l | 40 mmol/l |
| Glucose (g/l) | 1 g/l | 0 |

In summary, based on the above results, the inventors conclude that a bicarbonate-based solution can be prepared in a plastic material without $CO_2$ gas barrier, provided that the concentrates are adequately adjusted (pH levels and levels of ingredients).

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A multi-chamber container for storing a bicarbonate solution, the container comprising:
   a first chamber housing an alkaline bicarbonate concentrate, the alkaline bicarbonate concentrate having a pH ranging from 8.6 to 10.0; and
   a second chamber housing an acidic concentrate, the acidic concentrate having a pH ranging from about 1.0 to 3.0.

2. The multi-chamber container of claim 1 wherein the acidic concentrate has a pH effective to obtain, when the alkaline bicarbonate concentrate is mixed with the acidic concentrate, a mixed solution having a pH ranging from about 6.5 to 7.6.

3. The multi-chamber container of claim 1 wherein each of the chambers is constructed from a gas permeable material.

4. The multi-chamber container of claim 1 wherein the alkaline bicarbonate solution comprises: sodium chloride; sodium lactate; and sodium bicarbonate.

5. The multi-chamber container of claim 1 wherein the acidic concentrate comprises: glucose; calcium chloride; magnesium chloride; and an acid.

6. A method for stabilizing bicarbonate solutions, the method comprising the step of:
   housing an alkaline bicarbonate concentrate in a first container, adjusting the pH of the alkaline bicarbonate concentrate to a range of about 8.6 to 10.0;
   housing an acidic concentrate in the second container, and adjusting the acidic concentrate to a pH ranging from about 1.0 to 3.0.

7. The method of claim 6 wherein the step of adjusting the acidic concentrate is further defined by adjusting the acidic concentrate to a pH effective to obtain, when the alkaline bicarbonate concentrate is mixed with the acidic concentrate, a mixed solution having a pH ranging from about 6.5 to 7.6.

8. The method of claim 6 wherein the first container is a first chamber of a multi-chamber container and the second container is a second chamber of the multi-chamber container.

9. The method of claim 6 wherein the first and second containers are constructed from a gas permeable material.

10. The method of claim 6 further comprising the step of steam sterilizing the first and second containers.

11. The method of claim 6 wherein the alkaline bicarbonate solution comprises: sodium chloride; sodium lactate; and sodium bicarbonate.

12. The method of claim 6 wherein the acidic concentrate comprises: glucose; calcium chloride; magnesium chloride; and an acid.

13. The method of claim 6 wherein the step of adjusting the pH of the bicarbonate concentrate further comprises adding a physiologically acceptable base to the bicarbonate concentrate having an original pH of 8.0–8.4 to increase the pH thereto to the pH ranging from 8.6 to 10.

14. The method of claim 6 wherein the step of adjusting the pH of the acidic concentrate further comprises adding a physiologically acceptable acid to the acidic concentrate having an original pH of about 4.0–7.0 to decrease the pH of the acidic concentrate to the pH ranging from about 1.0 to 3.0.

* * * * *

UNITED STATES PATENT AND TRADEMARK OFFICE
CERTIFICATE OF CORRECTION

PATENT NO.    : 6,475,529 B2
DATED         : November 5, 2002
INVENTOR(S)   : Annick Duponchelle et al.

It is certified that error appears in the above-identified patent and that said Letters Patent is hereby corrected as shown below:

<u>Column 16,</u>
Line 11, delete "about".

Signed and Sealed this

Twenty-fifth Day of March, 2003

JAMES E. ROGAN
*Director of the United States Patent and Trademark Office*